(12) United States Patent
Lei et al.

(10) Patent No.: US 11,117,891 B2
(45) Date of Patent: Sep. 14, 2021

(54) ISOQUINOLIN AND NAPHTHYDRIN COMPOUNDS

(71) Applicant: Eli Lilly and Company, Indianapolis, IN (US)

(72) Inventors: Hui Lei, Shanghai (CN); Gang Liu, Shanghai (CN); Yuan Tian, Shanghai (CN); Haizhen Zhang, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/489,101

(22) PCT Filed: Feb. 21, 2018

(86) PCT No.: PCT/US2018/018949
§ 371 (c)(1),
(2) Date: Aug. 27, 2019

(87) PCT Pub. No.: WO2018/160406
PCT Pub. Date: Sep. 7, 2018

(65) Prior Publication Data
US 2020/0062751 A1  Feb. 27, 2020

(30) Foreign Application Priority Data
Feb. 28, 2017 (WO) ................ PCT/CN2017/075121

(51) Int. Cl.
*C07D 471/04* (2006.01)
*C07D 401/14* (2006.01)

(52) U.S. Cl.
CPC ......... *C07D 471/04* (2013.01); *C07D 401/14* (2013.01)

(58) Field of Classification Search
CPC .. C07D 471/04; C07D 401/14; C07D 401/04; A61P 37/02; A61P 31/12; A61P 1/16
See application file for complete search history.

(56) References Cited

U.S. PATENT DOCUMENTS

| | | | |
|---|---|---|---|
| 10,787,435 B2* | 9/2020 | Wu | A61K 31/43 |
| 2011/0009410 A1 | 1/2011 | Corkey et al. | |
| 2015/0342943 A1 | 12/2015 | Bornstein et al. | |

OTHER PUBLICATIONS

Hayakawa, Proc Jpn Acad, Ser. B, vol. 88, 434-453, 2012. (Year: 2012).*
Wang, Nature Medicine, vol. 23(4), Apr. 2017, 439-449. (Year: 2017).*
International Search Report of the International Searching Authority pertaining to International Application No. PCT/US2018/018949; dated May 4, 2018.
Written Opinion of the International Searching Authority pertaining to International Application No. PCT/US2018/018949; dated May 4, 2018.

* cited by examiner

*Primary Examiner* — D Margaret M Seaman
(74) *Attorney, Agent, or Firm* — Macharri R. Vorndarn-Jones

(57) ABSTRACT

The present invention provides a compound of Formula II wherein X is selected from the group consisting of CH and N; Q is selected from the group consisting of CH3 and H; R is selected from the group consisting of and; or a pharmaceutically acceptable salt thereof, compositions, methods to treat liver disease and NASH.

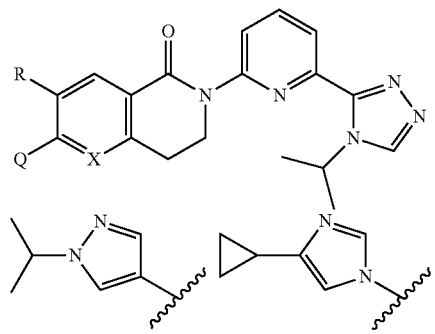

8 Claims, No Drawings

ISOQUINOLIN AND NAPHTHYDRIN COMPOUNDS

This invention provides isoquinolin and naphthydrin compounds or pharmaceutically acceptable salts thereof, and for use of the compounds in therapy. Isoquinolin and naphthydrin compounds of this invention are inhibitors of apoptois signal-regulating kinase 1 (ASK1).

ASK1 is a member of the large mitogen-activated protein kinase kinase kinase ("MAP3K") family.ASK1 activation and signaling are associated with broad range of diseases. Compounds that inhibit ASK1 are desired for use in the treatment of ASK1 mediated conditions.

Compounds that inhibit ASK1 are desired for use in the treatment of Nonalcoholic steatohepatitis (NASH). Nonalcoholic steatohepatitis is a liver disease with an etiological constellation characterized by macrovesicular hepatic steatosis, inflammation hepatocyte ballooning and fibrosis. Currently, there is no approved pharmaceutical medicament specifically for the treatment of nonalcoholic steatohepatitis. There is a need for pharmaceutical medicaments to offer additional treatment options for patients suffering from nonalcoholic steatohepatitis.

U.S. Pat. No. 8,742,126 discloses 5-(4-cyclopropyl-1H-imidazol-1-yl)-N-(6-(4-isopropyl-4H-1,2,4-triazol-3-y-l) pyridin-2-yl)-2-fluoro-4-methylbenzamide as an ASK1 inhibitor.

U.S. Patent Application Publication No. US 2015/0342943 discloses a method of preventing and/or treating liver disease using an ASK1 inhibitor.

There is a need for compounds that have ASK1 inhibitory activity.

The present invention provides a compound of Formula I

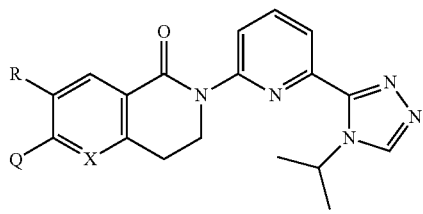

I wherein
X is selected from the group consisting of CH and N;
Q is selected from the group consisting of CH$_3$ and H;
R is selected from the group consisting of

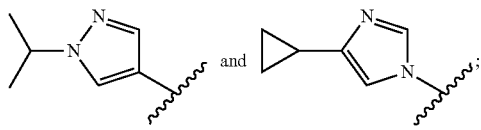

or
a pharmaceutically acceptable salt thereof.
In an embodiment, X is CH and Q is CH$_3$.
In an embodiment, X is N and Q is H.

In an embodiment X is CH; Q is CH$_3$; and R is

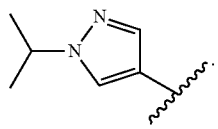 [SMILES: *c1cnn(C(C)C)c1]

In an embodiment X is CH; Q is CH$_3$; and R is

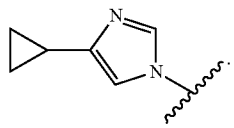 [SMILES: *n1cnc(C2CC2)c1]

In an embodiment X is N; Q is H; and R is

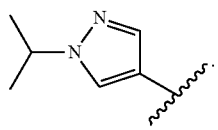 [SMILES: *c1cnn(C(C)C)c1]

In an embodiment X is N; Q is H; and R is

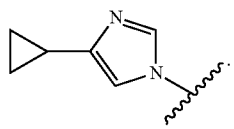 [SMILES: *n1cnc(C2CC2)c1]

In an embodiment the compound of Formula I is 7-(4-Cyclopropylimidazol-1-yl)-2-[6-(4-isopropyl-1,2,4-triazol-3-yl)-2-pyridyl]-6-methyl-3,4-dihydroisoquinolin-1-one or a pharmaceutically acceptable salt thereof.

In an embodiment the compound of Formula I is 3-(4-Cyclopropylimidazol-1-yl)-6-[6-(4-isopropyl-1,2,4-triazol-3-yl)-2-pyridyl]-7,8-dihydro-1,6-naphthyridin-5-one, or a pharmaceutically acceptable salt thereof.

The present invention provides a pharmaceutical composition comprising a compound of Formula I, or a pharmaceutically acceptable salt thereof, together with one or more pharmaceutically acceptable carriers, diluents, or excipients.

The present invention provides a method for treating a condition mediated by ASK1 activity comprising administering to the mammal in need of treatment, an effective amount of a compound of Formula I, or a pharmaceutically acceptable salt thereof. The present invention also provides a method for treating liver disease, comprising administering to a mammal in need thereof, an effective amount of a compound of Formula I, or a pharmaceutically acceptable salt thereof. The present invention provides a method for treating nonalcoholic steatohepatitis (NASH), comprising administering to a mammal in need thereof, an effective amount of a compound of Formula I, or a pharmaceutically acceptable salt thereof.

In another embodiment, the present invention provides a compound of Formula I, or a pharmaceutically acceptable salt thereof, for use in therapy. Further, provided is a compound of the present invention, or a pharmaceutically acceptable salt thereof or pharmaceutical composition, for use in the treatment of liver disease. Further, provided is a compound of the present invention, or a pharmaceutically acceptable salt thereof or pharmaceutical composition, for use in the treatment of NASH.

In another embodiment, provided is a compound of Formula I, or a pharmaceutically acceptable salt thereof, for use in the manufacture of a medicament for the treatment of liver disease. Preferably the medicament is for the treatment of NASH.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington: The Science and Practice of Pharmacy* (L. V. Allen, Editor, 22$^{nd}$ Edition, Pharmaceutical Press, 2012).

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002)

A human is a preferred mammal. As used herein, "patient" refers to a mammal in need of treatment. As used herein, the term "effective amount" or "therapeutically effective amount" of a compound refers to an amount, or a dosage, which is effective in treating a disorder or a disease, such as NASH, chronic kidney disease, or diabetic nephropathy as described herein. The attending diagnostician, as one skilled in the art, can readily determine an effective amount by the use of conventional techniques and by observing results obtained under analogous circumstances. In determining the effective amount or dose of a compound, a number of factors are considered, including but not limited to, the compound to be administered; the co-administration of other agents, if used; the species of mammal; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

The pharmaceutical composition is administered to a patient in amounts effective to treat liver disease, more particularly, NASH. An appropriate amount or dose effective to treat a patient can be determined by a health care provider.

The terms "treatment" and "treating" as used herein are intended to refer to all processes wherein there may be a slowing, interrupting, arresting, controlling, or stopping of the progression of an existing disorder and/or symptoms thereof, but does not necessarily indicate a total elimination of all symptoms.

The term "liver disease" as used herein embraces liver conditions or symptoms associated with ASK1 mediation, for example, metabolic liver disease, steatosis, liver fibrosis, primary sclerosing cholangitis (PSC), cirrhosis, liver fibrosis, non-alcoholic fatty liver disease (NAFLD), nonalcoholic steatohepatitis (NASH), hepatic ischemia reperfusion injury, and primary biliary cirrhosis (PBC).

The term "pharmaceutically acceptable carrier, diluent, or excipients" means that the carrier, diluent, and excipients are pharmaceutically compatible with the other ingredients of the composition. In a particular embodiment, the pharmaceutical compositions are formulated as a tablet or capsule for oral administration. The tablet or capsule can include a compound of the present invention in an amount effective to treat liver disease, particularly NASH.

The abbreviations used herein are defined according to Aldrichimica Acta, Vol. 17, No. 1, 1984. Other abbreviations are defined as follows: "ACN" refers to acetonitrile; "ADP" refers to adenosine diposphate; "AIBN" refers to azobisisobutyronitrile; "ATP" refers to adenosine triphosphate; "BSA" refers to Bovine Serum Albumin; "DCM" refers to dichloromethane; "DMEDA" refers to N,N'-dimethylethylenediamine; "DMEM" refers to Dulbecco's Modified Eagle's Medium; "DMF" refers to dimethylformamide; "DMSO" refers to dimethylsulfoxide; "DTT" refers to dithiothreitol; "EtOH" refers to ethanon or ethyl alcohol; "FA" refers to formic acid; "FBS" refers to Fetal Bovine Serum; "HEK" refers to human embryonic kidney; "HPLC" refers to high performance liquid chromatography; "IC$_{50}$" refers to the concentration of an agent that produces 50% of the maximal inhibitory response possible for that agent; "MAP" refers to mitogen-activated protein; "MeOH" refers to methanol or methyl alcohol; "MOPS" refers to (3-(N-morpholino)propanesulfonic acid); "NBS" refers to N-bromosuccinimide; "NIS" refers to N-iodosuccininude; "NP-40 refers to Tergitol-type NP-40 which is nonyl phenoxypolyethoxylethanoll; "pASK1" refers to phosphorylated ASK1; "PE" refers to petroleum ether; "TBAF" refers to tetra-n-butylammonium fluoride; "TFA" refers to trifluoroacetic acid; "THF" refers to tetrahydrofuran; "TMSCN" refers to trimethylsilyl cyanide; "t$_{(R)}$" refers to retention time.

The intermediates described in the following preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

The compounds of the present invention, or salts thereof, may be prepared by a variety of procedures known in the art, some of which are illustrated in the Preparations and Examples below. The specific synthetic steps for each of the routes described may be combined in different ways, to prepare compounds of the invention, or salts thereof. The products of each step can be recovered by conventional methods well known in the art, including extraction, evaporation, precipitation, chromatography, filtration, trituration, and crystallization. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

All substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

PREPARATIONS AND EXAMPLES

Preparation 1

6-Aminopyridine-2-carbohydrazide

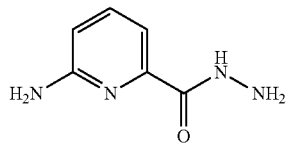 [SMILES: NNC(=O)c1cccc(N)n1]

To a solution of methyl 6-aminopyridine-2-carboxylate (145 g, 953 mmol) in MeOH (1.5 L) is added hydrazine hydrate (118 g, 2310 mmol). The reaction mixture is stirred at 75° C. under a nitrogen atmosphere for 16 hours. The mixture is cooled to room temperature and the precipitate is collected by filtration and dried under vacuum to give the title compound (130 g, 89.7%) as a white solid. $^1$H NMR (400 MHz, d$_6$-DMSO) δ 9.15 (br, 1H), 7.51 (t, J=7.8 Hz, 1H), 7.10 (d, J=7.2 Hz, 1H), 6.60 (d, J=8.4 Hz, 1H), 6.07 (br, 2H), 4.47 (br, 2H).

Preparation 2

N,6-Bis[(E)-dimethylaminomethyleneamino]pyridine-2-carboxamide

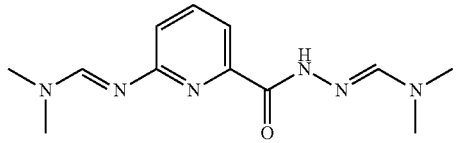

A mixture of 6-aminopyridine-2-carbohydrazide (65.0 g, 427 mmol) in N,N-dimethylformamide dimethyl acetal (600 g, 5040 mmol) is stirred at 95° C. for 16 hours. The mixture is cooled to room temperature and concentrated under reduced pressure to give a yellow residue. The residue is suspended in EtOAc (300 mL) and stirred for 30 minutes at 25° C. The resulting precipitate is collected by filtration and dried under vacuum to give the title compound (95.0 g, 84.8%) as white solid. $^1$H NMR (400 MHz, d$_6$-DMSO) δ 8.85 (s, 1H), 8.06 (s, 1H), 7.68 (t, J=7.6 Hz, 1H), 7.50-7.45 (m, 1H), 6.91 (d, J=7.6 Hz, 1H), 3.13 (s, 3H), 3.00 (s, 3H), 2.86 (s, 6H)

Preparation 3

6-(4-Isopropyl-1,2,4-triazol-3-yl)pyridin-2-amine

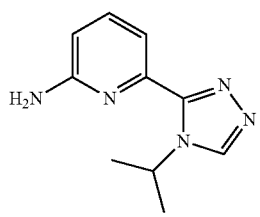

To a solution of N,6-bis[(E)-dimethylaminomethyleneamino]pyridine-2-carboxamide (105.0 g, 360 mmol) in ACN (450 mL) and acetic acid (120 mL) is added propan-2-amine (100 g, 1690 mmol) in portions maintaining the temperature below 30° C. The resulting mixture is stirred at 110° C. for 60 hours. The reaction mixture is cooled to 25° C., and the solvent is removed under reduced pressure. The residue is dissolved in water (500 mL) and the pH is adjusted ~10 with aqueous NaOH (1 N). The resulting precipitate is collected by filtration and is dissolved in DCM (500 mL), dried over anhydrous Na$_2$SO$_4$, and concentrated under reduced pressure to give an off white residue. The residue is suspended in EtOAc (100 mL), stirred for 15 minutes, and PE (200 mL) is slowly added. The resulting precipitate is collected by filtration and dried under vacuum to give the title compound (47.0 g, 62.9%) as an off-white solid. ES/MS (m/z): 204.1 (M+H), LCMS: t$_{(R)}$=0.565 min in 0-30% A to B, (Xtimate C18, 2.1*30 mm, 3 μm). $^1$H NMR (400 MHz, CD$_3$OD) δ 8.75 (s, 1H), 7.57 (t, J=8.0 Hz, 1H), 7.20 (d, J=7.2 Hz, 1H), 6.65 (d, J=8.0 Hz, 1H), 5.52 (spt, J=6.8 Hz, 1H), 1.52 (d, J=6.8 Hz, 6H).

Preparation 4

2-Chloro-6-(4-isopropyl-1,2,4-triazol-3-yl)pyridine

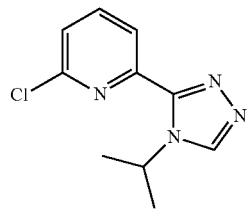

To a suspension of 6-(4-isopropyl-1,2,4-triazol-3-yl)pyridin-2-amine (60.0 g, 289.2 mmol) in DCM (1200 mL) is added benzyltriethylammonium chloride (133.2 g, 578.4 mmol), followed by drop-wise addition of tert-butyl nitrite (124.8 g, 1156.8 mmol) at 0° C. The mixture is warmed to 30° C. and stirred for 17 hours. The reaction is quenched by addition of aq. NaHCO$_3$ (1200 mL) solution and the product is extracted with DCM (3×1500 mL). The organic extracts are washed with brine, dried over Na$_2$SO$_4$, and concentrated in vacuo to give the crude product (64.363 g, 289.2 mmol) as a yellow solid. The material is purified by silica gel flash chromatography, eluting with a gradient of 0% to 1% MeOH in DCM to give the title compound (36.4 g, 52.6%) as a brown solid. ES/MS m/z: ($^{35}$Cl/$^{37}$Cl) 223.0/225.0 (M+H). $^1$H NMR (400 MHz, CDCl$_3$) δ 8.37 (s, 1H), 8.26 (dd, J=0.8, 7.8 Hz, 1H), 7.80 (t, J=7.8 Hz, 1H), 7.38 (dd, J=0.8, 7.8 Hz, 1H), 5.67-5.57 (m, 1H), 1.59-1.54 (m, 6H) and $^{13}$CNMR (100 MHz, CDCl$_3$) δ=150.63, 150.03, 148.31, 142.49, 139.82, 124.72, 122.38, 49.18, 23.72.

Preparation 5

2-Bromo-6-(4-isopropyl-1,2,4-triazol-3-yl)pyridine

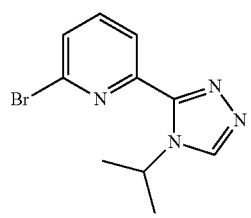

To a solution of 6-(4-isopropyl-1,2,4-triazol-3-yl)pyridin-2-amine (10.0 g, 48.2 mmol) in dibromomethane (150 mL) is added benzyltriethylammonium bromide (45.3 g, 193 mmol) and tert-butyl nitrite (49.7 g, 482 mmol) at 25° C. The mixture is stirred at 25° C. for 6 hours. The reaction is quenched by the addition of aq. NaHCO$_3$ (30 mL) solution and the product is extracted with DCM (150 mL). The organic extracts are washed with brine (15 mL), dried over Na$_2$SO$_4$, and concentrated in vacuo. The residue is purified by silica gel flash chromatography, eluting with a gradient of 2.5% to 3.3% MeOH in DCM to give the title compound (5.4 g, 37.7%) as a yellow solid. $^1$H NMR (400 MHz, CDCl$_3$) δ 8.30 (s, 1H), 8.26-8.18 (m, 1H), 7.67-7.61 (m, 1H), 7.47 (d, J=8.0 Hz, 1H), 5.63-5.41 (m, 1H), 1.50 (d, J=7.2 Hz, 6H)

Preparation 6

6-Bromo-3,4-dihydro-2H-isoquinolin-1-one

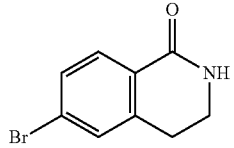 [SMILES: O=C1NCCc2cc(Br)ccc21]

MeSO$_3$H (118 g, 1220 mmol, 80.0 mL) is added to a mixture of 5-bromoindan-1-one (25.0 g, 118 mmol) in DCM (200 mL) at 0° C. NaN$_3$ (7.78 g, 118 mmol) is added slowly in portions to this mixture. The mixture is then stirred for an additional 30 minutes. The reaction mixture is stirred at 22° C. for 16 hours. The pH is adjusted to 10 with an aqueous mixture of NaOH (20% wt). The mixture is extracted with DCM (3×450 mL), the organic extracts are combined, dried over MgSO$_4$, and the solvent is removed under reduced pressure to give the crude material as a yellow oil. The residue is purified by silica gel flash chromatography, eluting with a gradient of 0% to 50% EtOAc in PE to give the title compound (19.0 g, 34.8%) as a yellow solid. ES/MS m/z ($^{79}$Br/$^{81}$Br): 225.8/227.8 (M+H), $^1$H NMR (400 MHz, CDCl$_3$) δ 7.91 (d, J=8.0 Hz, 1H), 7.48 (dd, J=1.8, 8.3 Hz, 1H), 7.39 (s, 1H), 6.84 (br s, 1H), 3.57 (dt, J=2.8, 6.7 Hz, 2H), 2.98 (t, J=6.5 Hz, 2H).

Preparation 7

6-Methyl-3,4-dihydro-2H-isoquinolin-1-one

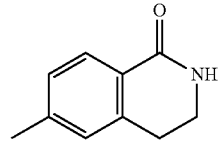

To a mixture of 6-bromo-3,4-dihydro-2H-isoquinolin-1-one (19.0 g, 82.4 mmol), CH$_3$B(OH)$_2$ (20.8 g, 329 mmol) and Na$_2$CO$_3$ (18.4 g, 165 mmol) in 1,4-dioxane (200 mL) and water (10.0 mL) is added [1,1'-bis(diphenylphosphino)ferrocene]dichloropalladium (II) (2.46 g, 3.29 mmol) under a nitrogen atmosphere and the mixture is stirred at 105° C. for 16 hours under a nitrogen atmosphere. The suspension is filtered through a pad of diatomaceous earth and the filter cake is washed with DCM (3×250 mL). The combined filtrates are washed with water (100 mL) and brine (80 mL), dried over Na$_2$SO$_4$, and the solvent is evaporated under reduced pressure. The crude product is purified by silica gel flash chromatography, eluting with a gradient of 0% to 50% EtOAc in PE to give the title compound (13.0 g, 95.2%) as a yellow solid. ES/MS (m/z): 162.0 (M+H), $^1$H NMR (400 MHz, CDCl$_3$) δ 7.94 (d, J=8.0 Hz, 1H), 7.15 (d, J=7.8 Hz, 1H), 7.02 (s, 1H), 6.89 (br s, 1H), 3.55 (dt, J=2.9, 6.6 Hz, 2H), 2.94 (t, J=6.5 Hz, 2H), 2.37 (s, 3H).

Preparation 8

7-Iodo-6-methyl-3,4-dihydro-2H-isoquinolin-1-one

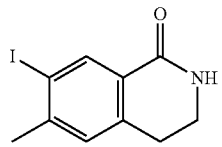

To a suspension of 6-methyl-3,4-dihydro-2H-isoquinolin-1-one (10.0 g, 60.3 mmol) in H$_2$SO$_4$ (200 mL) is added NIS (14.0 g, 60.3 mmol) slowly in portions at −10° C. and the reaction mixture is stirred at −10° C. for 30 minutes. The reaction mixture is poured into ice-water (450 mL) and the solution is extracted with EtOAc (3×600 mL). The combined organic extracts are washed with saturated NaHCO$_3$ solution and brine, dried over Na$_2$SO$_4$, filtered, and concentrated to a residue. The residue is purified by silica gel flash chromatography, eluting with a gradient of 0% to 50% EtOAc in PE to give the title compound (22.0 g) as a yellow solid. The solid is triturated with MeOH/DCM=1/20 (300 mL) and filtered to give the title compound (7.54 g, 33.0%) as a white solid. ES/MS (m/z): 288.0 (M+H), $^1$H NMR (400 MHz, CDCl$_3$) δ 8.45 (s, 1H), 7.09 (s, 1H), 6.93 (br s, 1H), 3.54 (dt, J=2.8, 6.7 Hz, 2H), 2.89 (t, J=6.7 Hz, 2H), 2.44 (s, 3H).

Preparation 9

7-(1-Isopropylpyrazol-4-yl)-6-methyl-3,4-dihydro-2H-isoquinolin-1-one

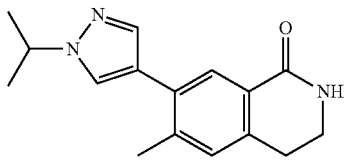 [SMILES: Cc1cc2c(cc1-c1cnn(C(C)C)c1)C(=O)NCC2]

To a solution of 7-iodo-6-methyl-3,4-dihydro-2H-isoquinolin-1-one (178.0 mg, 0.5890 mmol) in 1,4-dioxane (5.5 mL) and water (0.7 mL) is added 1-isopropyl-4-(4,4,5,5-tetramethyl-1,3,2-dioxaborolan-2-yl)pyrazole (0.1147 g, 0.4712 mmol), 1,1'-bis(diphenylphosphino)ferrocene-palladium(II) dichloride dichloromethane complex (0.0491 g, 0.0589 mmol) and K$_2$CO$_3$ (0.163 g, 1.178 mmol). The mixture is de-gassed with nitrogen and stirred at 100° C. for 2 hours under microwave conditions. The mixture is filtered via a 2 cm silica gel cartridge and the solvent is removed in vacuo. The residue is purified by silica gel flash chromatography, eluting with a gradient of 0% to 4% MeOH in DCM to give the title compound (142.0 mg, 85.05%) as yellow oil. ES/MS (m/z): 270.2 (M+H).

Preparation 10

7-(4-Cyclopropylimidazol-1-yl)-6-methyl-3,4-dihydro-2H-isoquinolin-1-one

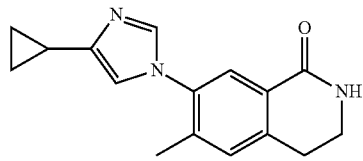 [SMILES: Cc1cc2c(cc1-n1cnc(C3CC3)c1)C(=O)NCC2]

To a suspension of 7-iodo-6-methyl-3,4-dihydro-2H-isoquinolin-1-one (446.0 mg, 1.476 mmol), 4-cyclopropyl-1H-imidazole (218.4 mg, 1.919 mmol) in DMSO (2.5 mL) is added $K_2CO_3$ (0.408 g, 2.952 mmol). The mixture is degassed with a stream of $N_2$ for 5 minutes. L-Proline (0.034 g, 0.295 mmol) and CuI (0.0562 g, 0.295 mmol) are added sequentially and the resulting mixture is stirred at 130° C. for 5 hours under microwave conditions. The reaction mixture is slowly quenched with water (30 mL). The aqueous phase is extracted with EtOAc (2×80 mL) and washed with saturated brine (25 mL). The organic extracts are dried over $Na_2SO_4$, filtered, and evaporated to dryness. The crude product is purified by silica gel flash chromatography, eluting with a gradient of 0% to 4% MeOH in DCM to give the title compound (0.198 g, 47.68%) as a white solid. ES/MS (m/z): 268.0 (M+H).

Preparation 11

Ethyl 5-bromo-2-(bromomethyl)pyridine-3-carboxylate

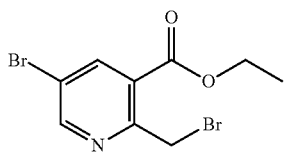

To a suspension of ethyl 5-bromo-2-methyl-pyridine-3-carboxylate (9.00 g, 36.9 mmol) and NBS (6.63 g, 37.2 mmol) in $CCl_4$ (100 mL) is added AIBN (605 mg, 3.69 mmol) under a $N_2$ atmosphere and the reaction mixture is stirred at 80° C. for 16 hours. The reaction is quenched with saturated aqueous $Na_2S_2O_3$ (200 mL) and the mixture is extracted with DCM (3×350 mL). The organic extracts are washed with brine, dried over $Na_2SO_4$, filtered, and concentrated under reduced pressure to a residue. The residue is purified by silica gel flash chromatography, eluting with a gradient of 0% to 5% EtOAc in PE to give the title compound (8.30 g, 64.8%) as a red semisolid. ES/MS ($^{79}Br/^{81}Br$): 321.8/323.8/325.8 (M+H), $^1H$ NMR (400 MHz, $CDCl_3$) δ 8.74 (d, J=2.5 Hz, 1H), 8.39 (d, J=2.5 Hz, 1H), 4.98 (s, 2H), 4.44 (q, J=7.4 Hz, 2H), 1.44 (t, J=7.0 Hz, 3H).

Preparation 12

Ethyl 5-bromo-2-(cyanomethyl)pyridine-3-carboxylate

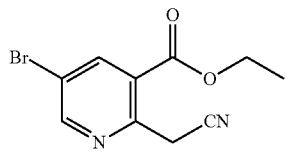

To a solution of ethyl 5-bromo-2-(bromomethyl)pyridine-3-carboxylate (7.20 g, 20.7 mmol) in $CH_3CN$ (100 mL) is added TBAF (1.0 mol/L) in THF (31.1 mL, 31.1 mmol) and TMSCN (3.15 g, 31.1 mmol) at 0° C. The reaction mixture is stirred at 20° C. for 2 hours. The mixture is washed with water (100 mL) and extracted with EtOAc (3×150 mL). The organic extracts are dried over $MgSO_4$, and the solvent is removed under reduced pressure. The residue is purified by silica gel flash chromatography, eluting with a gradient of 0% to 10% EtOAc in PE to give the title compound (5.00 g, 54.0%, about 65% purity) as a white semisolid. ES/MS m/z ($^{79}Br/^{81}Br$): 268.9/270.9 (M+H).

Preparation 13

3-Bromo-7,8-dihydro-6H-1,6-naphthyridin-5-one

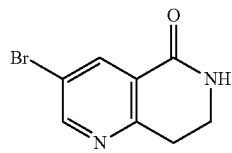

To a mixture of ethyl 5-bromo-2-(cyanomethyl)pyridine-3-carboxylate (4.64 g, 10.4 mmol, 60.2 mass %) in EtOH (150 mL) is added Raney-Ni (50 mass % in water, 0.464 g, 2.71 mmol). The mixture is stirred at 50° C. under hydrogen (103 kPa) for 2 hours. The suspension is filtered through a pad of diatomaceous earth and the filter cake is washed with EtOH (3×120 mL). The filtrate is concentrated and purified by silica gel flash chromatography, eluting with a gradient of 0% to 3.3% MeOH in DCM to give a residue (3.5 g) as a yellow solid. The material is further purified by Pre-HPLC: LC column: Phenomenex Synergi Max-RP 250×50 mm×10 μm; A: $H_2O$ (0.1% TFA); B: ACN, gradient: 5-35% B in A; column temperature: room temperature; flow rate: 110 mL/min. After Pre-HPLC purification, the eluent is evaporated to remove the organic solvents. The pH of the residual aqueous solution is adjusted with $Na_2CO_3$ (solid) to pH~10 and extracted with DCM (3×200 mL). The combined organic extracts are washed with $H_2O$ (100 mL) and brine (100 mL), dried over $Na_2SO_4$, filtered, and concentrated to give the title compound (800 mg, 31.2%) as a yellow solid. ES/MS m/z ($^{79}Br/^{81}Br$): 226.9/228.9 (M+H), LCMS: $t_{(R)}$=1.552 min, (Xtimate C18, 2.1×30 mm, 3 μm), $^1H$ NMR (400 MHz, $CDCl_3$) δ 8.69 (d, J=2.4 Hz, 1H), 8.45 (d, J=2.4 Hz, 1H), 6.50 (br s, 1H), 3.66 (dt, J=2.8, 6.8 Hz, 2H), 3.17 (t, J=6.8 Hz, 2H).

Preparation 14

3-(4-Cyclopropylimidazol-1-yl)-7,8-dihydro-6H-1,6-naphthyridin-5-one

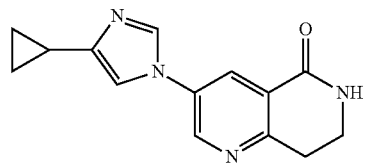 [SMILES: O=C1NCCc2ncc(-n3cnc(C4CC4)c3)cc21]

To a solution of 3-bromo-7,8-dihydro-6H-1,6-naphthyridin-5-one (0.100 g, 0.437 mmol) and 4-cyclopropyl-1H-imidazole (0.0709 g, 0.655 mmol) in DMF (5.00 mL) is added $K_2CO_3$ (0.181 g, 1.31 mmol). The mixture is degassed with a stream of $N_2$ for 5 minutes. DMEDA (0.0193 g, 0.218 mmol) and CuI (0.0832 g, 0.437 mmol) are added sequentially and the resulting mixture is stirred at 110° C. for 16 hours under $N_2$. The mixture is extracted with EtOAc (2×75 mL) and washed with saturated brine (3×25 mL). The organic extracts are dried over $Na_2SO_4$, filtered, and evaporated to dryness. The crude product is purified by silica gel flash chromatography, eluting with a gradient of 0% to 5% MeOH in DCM to give the title compound (0.060 g, 48.6%) as a light green solid. ES/MS (m/z): 255.0 (M+H), $^1$H NMR (400 MHz, $CDCl_3$) δ 8.74 (d, J=3.2 Hz, 1H), 8.33 (d, J=2.4 Hz, 1H), 7.81 (s, 1H), 7.10 (s, 1H), 6.31 (br s, 1H), 3.73 (dt, J=3.2, 6.8 Hz, 2H), 3.39-3.15 (m, 2H), 1.99-1.90 (m, 1H), 0.96-0.88 (m, 4H)

Preparation 15

3-(1-Isopropylpyrazol-4-yl)-7,8-dihydro-6H-1,6-naphthyridin-5-one

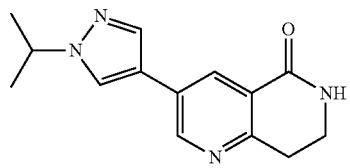 [SMILES: CC(C)n1cc(-c2cnc3c(c2)C(=O)NCC3)cn1]

To a solution of 3-bromo-7,8-dihydro-6H-1,6-naphthyridin-5-one (0.0750 g, 0.328 mmol) and 1-isopropyl-4-(4,4,5,5-tetramethyl-1,3,2-dioxaborolan-2-yl)pyrazole (0.116 g, 0.492 mmol) in 1,4-dioxane (4.00 mL) and water (1.00 mL) is added $Na_2CO_3$ (0.104 g, 0.983 mmol) and $Pd(PPh_3)_4$ (0.0759 g, 0.0655 mmol). The mixture is stirred at 110° C. for 16 hours under $N_2$. The mixture is extracted with DCM (2×75 mL) and washed with saturated brine (25 mL). The organic extracts are dried over $Na_2SO_4$, filtered, and evaporated to dryness. The crude product is purified by silica gel flash chromatography, eluting with a gradient of 0% to 3.3% MeOH in DCM to give the title compound (0.0800 g, 90.5%) as a white solid. $^1$H NMR (400 MHz, $CDCl_3$) δ 8.71 (d, J=2.0 Hz, 1H), 8.31 (d, J=2.0 Hz, 1H), 7.79 (s, 1H), 7.72 (s, 1H), 6.00 (br s, 1H), 4.49 (spt, J=6.8 Hz, 1H), 3.61 (dt, J=3.2, 6.4 Hz, 2H), 3.14 (t, J=6.4 Hz, 2H), 1.50 (d, J=6.8 Hz, 6H)

Example 1

7-(1-Isopropylpyrazol-4-yl)-2-[6-(4-isopropyl-1,2,4-triazol-3-yl)-2-pyridyl]-6-methyl-3,4-dihydroisoquinolin-1-one 2-Chloro-6-(4-isopropyl-1,2,4-triazol-3-yl)pyridine (150.4 mg, 0.6011 mmol), 7-(1-isopropylpyrazol-4-yl)-6-methyl-3,4-dihydro-2H-isoquinolin-1-one (142.0 mg, 0.501 mmol), XantPhos Pd G3 (0.05001 g, 0.05009 mmol), 4,5-bis(diphenylphosphino)-9,9-dimethylxanthene (XantPhos) (0.0299 g, 0.05009 mmol) and $Cs_2CO_3$ (0.2856 g, 0.8766 mmol) are added together with 1,4-dioxane (4.0 mL). The resulting mixture is heated to 110° C. and stirred for 3 hours under microwave conditions. The mixture is filtered via a 2 cm silica gel cartridge and the solvent is removed in vacuo. The residue is further purified by Pre-HPLC: LC column: SunFire C18 30×100 mm 5 m; A: $H_2O$ (0.1% FA); B: ACN (0.1% FA), gradient: 38-53% B in A at 0-10 min, stop at 17 min; column temperature: room temperature; flow rate: 30 mL/min, $t_{(R)}$=8.8 minutes (UV). The material is dissolved in water and lyophilized to give the title compound (130.0 mg, 54.11%) as a white solid. ES/MS (m/z): 456.3 (M+H).

Example 2

7-(4-Cyclopropylimidazol-1-yl)-2-[6-(4-isopropyl-1,2,4-triazol-3-yl)-2-pyridyl]-6-methyl-3,4-dihydroisoquinolin-1-one 2-Chloro-6-(4-isopropyl-1,2,4-triazol-3-yl)pyridine (99.2 mg, 0.397 mmol), 7-(4-cyclopropylimidazol-1-yl)-6-methyl-3,4-dihydro-2H-isoquinolin-1-one (93.0 mg, 0.331 mmol), XantPhos Pd G3 (0.033 g, 0.0331 mmol), 4,5-bis(diphenylphosphino)-9,9-dimethylxanthene (XantPhos) (0.0201 g, 0.0331 mmol) and $Cs_2CO_3$ (0.188 g, 0.578 mmol) are added together in 1,4-dioxane (3.0 mL). The resulting mixture is heated to 110° C. and stirred for 3 hours under microwave conditions. The mixture is filtered via a 2 cm silica gel cartridge and the solvent is removed in vacuo. The residue is further purified by Pre-HPLC: LC column: XBridge C18 30×100 mm 5 m; A: $H_2O$ (10 mM $NH_4HCO_3$); B: ACN, gradient: 27-42% B in A at 0-12 min, stop at 17 min; column temperature: room temperature; flow rate: 35 mL/min, $t_{(R)}$=7.9 minutes (UV). The material is dissolved in water and lyophilized to give the title compound (50.0 mg, 31.7%) as a white solid. ES/MS (m/z): 454.0 (M+H).

Example 3

3-(4-Cyclopropylimidazol-1-yl)-6-[6-(4-isopropyl-1,2,4-triazol-3-yl)-2-pyridyl]-7,8-dihydro-1,6-naphthyridin-5-one; hydrochloride

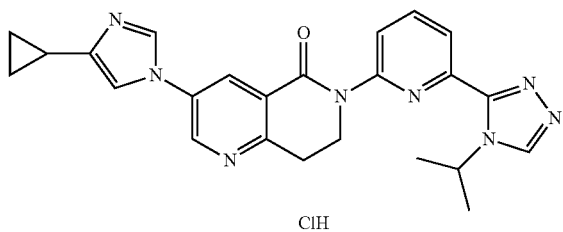 [SMILES: CC(C)n1cnnc1-c1cccc(N2CCc3ncc(-n4cnc(C5CC5)c4)cc3C2=O)n1 ; Cl]

ClH

A solution of 2-bromo-6-(4-isopropyl-1,2,4-triazol-3-yl)pyridine (0.0819 g, 0.276 mmol), 3-(4-cyclopropylimidazol-1-yl)-7,8-dihydro-6H-1,6-naphthyridin-5-one (0.060 g, 0.212 mmol) and $Cs_2CO_3$ (0.208 g, 0.637 mmol) in 1,4-dioxane (4.00 mL) is stirred for 1 minute under $N_2$. XantPhos (0.0368 g, 0.0637 mmol) and $Pd_2(dba)_3$ (0.0200 g, 0.0212 mmol) are added sequentially and the resulting mixture is stirred at 110° C. for 5 hours under $N_2$. The mixture is diluted with DCM (2×75 mL) and washed with saturated brine (25 mL). The organic layer is dried over $Na_2SO_4$, filtered, and evaporated to dryness. The crude product is purified by silica gel flash chromatography, eluting with a gradient of 0% to 5% MeOH in DCM to give a residue. The material is further purified by Pre-HPLC: LC column: YMC-Actus Triart C18 150×30 5 μm; A: $H_2O$ (0.05% HCl); B: ACN, gradient: 0-70% B in A; column temperature: room temperature; flow rate: 25 mL/min. The material is dissolved in water and lyophilized to give the title compound (0.0468 g, 44.6%) as a white solid. ES/MS (m/z): 441.0 (M+H), LCMS: $t_{(R)}$=1.303 min in 10-80% A to B, 4 min chromatography (Xtimate C18 2.1×30 mm), $^1$H NMR (400 MHz, $CD_3OD$) δ 9.84 (s, 1H), 9.52 (d, J=1.6 Hz, 1H), 9.09 (d, J=2.4 Hz, 1H), 8.78 (d, J=3.2 Hz, 1H), 8.25-8.21 (m, 1H), 8.17 (t, J=7.6 Hz, 1H), 8.11-8.07 (m, 1H), 7.97 (s, 1H), 5.70 (td, J=6.4, 13.2 Hz, 1H), 4.51 (t, J=6.4 Hz, 2H), 3.51 (t, J=6.4 Hz, 2H), 2.16-2.01 (m, 1H), 1.71 (d, J=6.4 Hz, 6H), 1.22-1.15 (m, 2H), 0.99-0.93 (m, 2H)

Example 4

3-(1-Isopropylpyrazol-4-yl)-6-[6-(4-isopropyl-1,2,4-triazol-3-yl)-2-pyridyl]-7,8-dihydro-1,6-naphthyridin-5-one

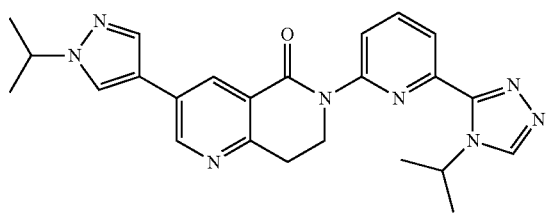 [SMILES: CC(C)n1cc(-c2cnc3c(c2)C(=O)N(c2cccc(-c4nncn4C(C)C)n2)CC3)cn1]

To a solution of 3-(1-isopropylpyrazol-4-yl)-7,8-dihydro-6H-1,6-naphthyridin-5-one (0.0800 g, 0.297 mmol) and 2-bromo-6-(4-isopropyl-1,2,4-triazol-3-yl)pyridine (0.114 g, 0.386 mmol) in 1,4-dioxane (6.00 mL) is added $Cs_2CO_3$ (0.242 g, 0.741 mmol). The mixture is degassed with a stream of $N_2$ for 5 minutes. XantPhos (0.0343 g, 0.0593 mmol) and $Pd_2(dba)_3$ (0.0280 g, 0.0297 mmol) are added sequentially and the resulting mixture is stirred at 110° C. for 3 hours under $N_2$. The mixture is extracted with DCM (2×75 mL) and washed with saturated brine (25 mL). The organic extracts are dried over $Na_2SO_4$, filtered, and evaporated to dryness. The crude product is purified by silica gel flash chromatography, eluting with a gradient of 0% to 5% MeOH in DCM. The residue is re-crystallized from water and $CH_3CN$ and dried by lyophilization to give the title compound (0.1165 g, 85.6%) as a light yellow solid. ES/MS (m/z): 443.1 (M+H), LCMS: $t_{(R)}$=1.918 min in 10-80% A to B A: $H_2O$ (0.05% HCl); B: ACN, 4 min chromatography (Xtimate C18 2.1*30 mm), $^1$H NMR (400 MHz, $CDCl_3$) δ 8.83 (d, J=2.4 Hz, 1H), 8.50 (d, J=2.4 Hz, 1H), 8.38 (s, 1H), 8.14 (d, J=7.2 Hz, 1H), 8.06-7.99 (m, 1H), 7.96-7.91 (m, 1H), 7.88 (s, 1H), 7.81 (s, 1H), 5.52 (quin, J=6.8 Hz, 1H), 4.62-4.52 (m, 1H), 4.36 (t, J=6.8 Hz, 2H), 3.35 (t, J=6.4 Hz, 2H), 1.58 (d, J=1.6 Hz, 6H), 1.57 (d, J=1.6 Hz, 6H)

Biological Assays

ASK1 Inhibitor Effect Determined by ASK1 Enzymatic Assay

The purpose of this assay is to determine the effect of ASK1 inhibitors on the production of ADP by ASK1. The recombinant human ASK1 (hASK1) catalytic domain tagged with Glutathione S-transferase is used, and histidine-tagged full-length human MAP kinase kinase 6 (MKK6) and ATP are the substrate and cofactor, respectively.

The assay is done using an ADP-Glo™ Kinase Assay Kit (Promega, Catalog #V9102) according to the manufacturer's protocol with the following modifications. Briefly, hASK1 (0.25 nM) and MKK6 (300 nM) in a buffer (10 mM MOPS pH 7.0; 10 mM Mg-Acetate; 1 mM DTT; 0.025% NP-40; 0.05% BSA; 1.5% glycerol) are incubated with ASK1 inhibitors at varying concentrations ranging from 10.00 uM to 0.17 nM for 15 minutes, followed by incubation with ATP (100 uM) for 30 minutes at room temperature. ADP-Glo™ Reagent is added to terminate the kinase reaction and deplete the remaining ATP. The Kinase Detection Reagent is then added to convert ADP to ATP. The newly synthesized ATP is measured using a luciferase/luciferin reaction, and the luminescence determined by Envision (PerkinElmer). The luminescence intensities are analyzed by GeneData, and fit to a 4 parameter dose response-inhibitor logistics curve to determine $IC_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle for 100% and 0% inhibition, respectively.

The compounds of Examples 1-4 herein are tested essentially as described above and exhibit $IC_{50}$ values as shown in Table 1 below.

TABLE 1

| Example # | hASK1 $IC_{50}$ (nM) | Efficacy (%) |
|---|---|---|
| 1 | 3.6 ± 0.8, n = 2 | 101 |
| 2 | 1.8 ± 0.4, n = 6 | 100.5 |

TABLE 1-continued

| Example # | hASK1 IC$_{50}$ (nM) | Efficacy (%) |
|---|---|---|
| 3 | 3.8 ± 0.9, n = 6 | 100.1 |
| 4 | 4.2 ± 0.8 n = 2 | 99.8 |

Mean ± standard deviation

These results indicate that the compounds of Examples 1-4 inhibit ASK1 enzymatic activity as shown in Table 1.

ASK1 Inhibitor Effect Determined by ASK1 Autophosphorylation (Thr838) Assay

The purpose of this assay is to determine the effect of ASK1 inhibitors on H$_2$O$_2$-stimulated ASK1 autophosphorylation at Thr838 in HEK293 cells overexpressing human ASK1.

HEK293 cells overexpressing human influenza hemagglutinin-(HA-) tagged full length human ASK1 are maintained in DMEM supplemented with 10% FBS at 37° C. and 5% CO$_2$. For the assay, the cells are plated in matrigel-coated 96-well plates (25,000 cells/well) and incubated overnight. The cells are treated with ASK1 inhibitors at varying concentrations ranging from 10.00 µM to 0.17 nM for 1 hour, followed by stimulation with 1 mM H$_2$O$_2$ for 10 minutes. The cells are then lysed with Homogeneous Time-Resolved Fluorescence (HTRF®) lysis buffer (Cisbio, Catalog #64KL1FDF) containing phosphatase inhibitors (ThermoFisher, Catalog #78430). pASK1 is quantified by HTRF®, using an anti-HA and anti-pASK1 (Thr838) antibody pair customized by Cisbio, on Envision (PerkinElmer) with emission and excitation wavelengths of 620 and 665 nm, respectively. The ratios of fluorescence intensities at 665 nm and 620 nm are analyzed by GeneData, and fit to a 4 parameter dose response-inhibitor logistics curve to determine IC$_{50}$ values, using the effects of 5-(4-cyclopropyl-1H-imidazol-1-yl)-2-fluoro-4-methyl-N-{6-[4-(propan-2-yl)-4H-1,2,4-triazol-3-yl]pyridin-2-yl}benzamide as a standard and DMSO vehicle as 100% and 0% inhibition, respectively.

The compounds of Example 1-4 herein are tested essentially as described above and exhibit IC$_{50}$ values as shown in Table 2 below.

TABLE 2

| Example # | HEK pASK1 IC$_{50}$ (nM) | Efficacy (%) |
|---|---|---|
| 1 | 38.6 ± 2.4, n = 2 | 107 |
| 2 | 13.1 ± 2.8, n = 2 | 103 |
| 3 | 31.5 ± 6.6, n = 2 | 107 |
| 4 | 41.9 ± 0.5, n = 2 | 105 |

Mean ± standard deviation

These results indicate that the compounds of Examples 1-4 inhibit H$_2$O$_2$-stimulated ASK1 autophosphorylation at Thr838 in HEK293 cells as shown in Table 2 above.

We claim:
1. A compound of the formula

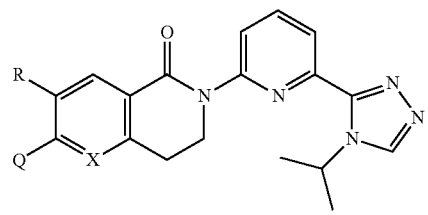

wherein
X is N;
Q is selected from the group consisting of CH$_3$ and H;
R is selected from the group consisting of

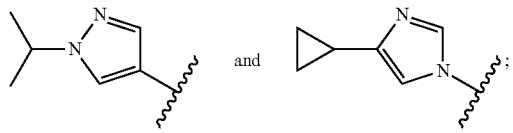

or
a pharmaceutically acceptable salt thereof.

2. A compound as claimed by claim 1 wherein Q is H.
3. A compound as claimed by claim 1 wherein Q is CH$_3$.
4. A compound as claimed by claim 1 wherein R is

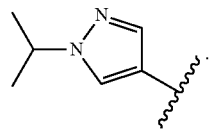 [SMILES: *c1cnn(C(C)C)c1]

5. A compound as claimed by claim 1 to wherein R is

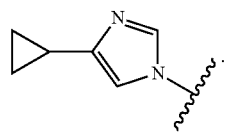 [SMILES: *n1cnc(C2CC2)c1]

6. A compound as claimed by claim 1 wherein the compound is 3-(4-Cyclopropylimidazol-1-yl)-6-[6-(4-isopropyl-1,2,4-triazol-3-yl)-2-pyridyl]-7,8-dihydro-1,6-naphthyridin-5-one, or a pharmaceutically acceptable salt thereof.

7. A pharmaceutical composition comprising a compound as claimed by claim 1, or a pharmaceutically acceptable salt thereof, and at least one selected from the group consisting of a pharmaceutically acceptable carrier, diluent, and excipient.

8. A method for treating nonalcoholic steatohepatitis (NASH), comprising administering to a mammal in need thereof, an effective amount of a compound as claimed by claim 1, or a pharmaceutically acceptable salt thereof.

* * * * *

UNITED STATES PATENT AND TRADEMARK OFFICE
CERTIFICATE OF CORRECTION

PATENT NO. : 11,117,891 B2
APPLICATION NO. : 16/489101
DATED : September 14, 2021
INVENTOR(S) : Hui Lei et al.

Page 1 of 1

It is certified that error appears in the above-identified patent and that said Letters Patent is hereby corrected as shown below:

On the Title Page

Column 2, Line 2 (Item (74) Attorney, Agent, or Firm): Delete "Vorndarn-Jones" and insert -- Vorndran-Jones --, therefor.

Column 2 (Item (57) Abstract): Delete "II" and insert -- I --, therefor.

Column 2 (Item (57) Abstract): Delete "CH3" and insert -- $CH_3$ --, therefor.

In the Claims

Column 16, Line 39: In Claim 5, after "claim 1" delete "to".

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*